US010682326B1

(12) United States Patent
Pradeep et al.

(10) Patent No.: US 10,682,326 B1
(45) Date of Patent: Jun. 16, 2020

(54) STABLE MELPHALAN LIQUID INJECTABLE FORMULATIONS

(71) Applicants: Shivakumar Pradeep, Vizianagaram (IN); Krishnamurthy Toppaladoddi, Vizianagaram (IN); Rizwan Ahmed, Vizianagaram (IN); Guptha Chinni Guru Deva, Vizianagaram (IN); Nagaraju Dasari, Vizianagaram (IN)

(72) Inventors: Shivakumar Pradeep, Vizianagaram (IN); Krishnamurthy Toppaladoddi, Vizianagaram (IN); Rizwan Ahmed, Vizianagaram (IN); Guptha Chinni Guru Deva, Vizianagaram (IN); Nagaraju Dasari, Vizianagaram (IN)

(73) Assignee: SHILPA MEDICARE LIMITED, Raichur, Karnataka ( * ) Notice: Subject to any disclaimer, the term of this patent is extended or adjusted under 35 U.S.C. 154(b) by 1 day.

(21) Appl. No.: 16/513,758

(22) Filed: Jul. 17, 2019

(30) Foreign Application Priority Data

Jun. 3, 2019 (IN) .............................. 201941021913

(51) Int. Cl.
| *A61K 31/198* | (2006.01) |
| *A61K 47/10* | (2017.01) |
| *A61K 9/08* | (2006.01) |
| *A61K 9/10* | (2006.01) |
| *A61K 9/00* | (2006.01) |

(52) U.S. Cl.
CPC .......... *A61K 31/198* (2013.01); *A61K 9/0019* (2013.01); *A61K 9/08* (2013.01); *A61K 9/10* (2013.01); *A61K 47/10* (2013.01)

(58) Field of Classification Search
CPC ...... A61K 31/198; A61K 9/0019; A61K 9/10; A61K 47/10; A61K 9/08
See application file for complete search history.

(56) References Cited

U.S. PATENT DOCUMENTS

| 4,997,651 A | 3/1991 | Poole et al. |
| 2010/0311838 A1 | 12/2010 | Pipkin et al. |
| 2013/0131174 A1 | 5/2013 | Castillo et al. |
| 2014/0005148 A1 | 1/2014 | Neelakantan et al. |
| 2014/0213650 A1 | 7/2014 | Pipkin et al. |
| 2014/0221488 A1 | 8/2014 | Pipkin et al. |
| 2018/0193255 A1 | 7/2018 | Chandrashekhar et al. |

FOREIGN PATENT DOCUMENTS

RU 2060031 C1 5/1996

*Primary Examiner* — Robert S Cabral

(57) ABSTRACT

The present invention relates to a stable, non-aqueous liquid, formulation consisting essentially of melphalan, or a pharmaceutical acceptable salt thereof; and one or more solvents selected from group consisting of dimethyl acetamide, polyethylene glycol, ethanol, propylene glycol, dimethyl sulfoxide, N-methylpyrrolidone and glycerol; wherein said formulation is free of antioxidants, organic acid and added chloride ions; and the process for preparation thereof.

5 Claims, No Drawings

STABLE MELPHALAN LIQUID INJECTABLE FORMULATIONS

FIELD OF THE INVENTION

The present invention relates to the stable, non-aqueous liquid, formulation consisting essentially of melphalan, or a pharmaceutical acceptable salt thereof, preferably melphalan hydrochloride; and one or more solvents selected from group consisting of dimethyl acetamide, polyethylene glycol, ethanol, propylene glycol, dimethyl sulfoxide, N-methylpyrrolidone and glycerol; wherein said formulation is free of antioxidants, organic acid and added chloride ions; and wherein said formulation, following dilution with a pharmaceutically acceptable diluent, is suitable for injection into a patient. Further this invention also describes process of preparing such formulations.

BACKGROUND OF THE INVENTION

Melphalan, also known as L-phenylalanine mustard, L-PAM or L-sarcolysin, is a phenyl alanine derivative of nitrogen mustard. Melphalan is a bifunctional alkylating agent that is active against selected human neoplastic diseases. Melphalan is structurally represented as

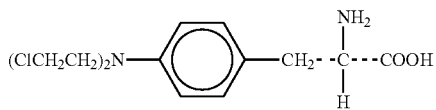

Melphalan is commercially supplied as freeze-dried or lyophilized powder with the brand names Alkeran® and Evomela®. Alkeran® for injection is supplied as a sterile, non-pyrogenic freeze-dried powder, where each vial of Alkeran® for injection contains melphalan hydrochloride equivalent to 50 mg of melphalan and 20 mg povidone. Alkeran® for injection is reconstituted with the sterile diluent provided that contains sodium citrate 0.2 g, propylene glycol 6.0 mL, ethanol (96%) 0.52 mL and water for injection to total of 10 mL. Alkeran® for injection is reconstituted with 10 mL of sterile diluent to provide a 5 mg/mL solution which is further diluted in 0.9% sodium chloride injection to have a concentration of not greater than 0.45 mL and administered intravenously over a period of minimum 15 minutes for the palliative treatment of patients with multiple myeloma for whom oral therapy is not appropriate.

Evomela® for injection is supplied as a sterile white-to-off white lyophilized powder in a single-dose vial for intravenous use. Each vial of Evomela® contains 50 mg melphalan free base equivalent to 56 mg melphalan hydrochloride and 2700 mg Betadex Sulfobutyl Ether Sodium NF. Evomela® vial is reconstituted with 8.6 mL of 0.9% sodium chloride injection to make a 50 mg/10 mL (5 mg/mL) nominal concentration of melphalan, which is further diluted with appropriate amount of 0.9% sodium chloride injection to a final concentration of 0.45 mg/mL and administered intravenously over a period of 15 to 20 minutes for the palliative treatment of patients with multiple myeloma for whom oral therapy is not appropriate and over a period of 30 minutes for high-dose conditioning treatment prior to hematopoietic progenitor (stem) cell transplantation in patients with multiple myeloma.

U.S. Pat. No. 4,997,651 discloses a pharmaceutical formulation of melphalan comprising as two separate components (a) freeze-dried melphalan hydrochloride, and (b) a solvent-diluent comprising a citrate, propylene glycol and ethanol.

US Patent Application Nos. 2010/031138, 2014/0213650 and 2014/0221488 disclose parenteral compositions comprising melphalan and a cyclodextrin derivative.

US Patent Application No. 2013/0131174 discloses a solid lyophilization composition of melphalan hydrochloride and a pH buffer solution, further comprising a sterile solution of sodium chloride at a concentration of between 0% and 10% providing a reconstitution composition of said melphalan hydrochloride lyophilized, said reconstitution composition being free of organic solvents.

RU 2060031 discloses parenteral lyophilized formulation comprising a melphalan, polyvinylpyrrolidone, ascorbic acid, glutamic acid, hydrochloric acid, and D-mannitol.

As the reconstitution of the lyophilized product is clinically inconvenient and the lyophilization process is time consuming the inventors of US Patent Application Nos. 2014/0005148 and US 2018/0193255 have developed the liquid formulation compositions of melphalan.

US Patent Application No. 2014/0005148 (US '148 Application) discloses the stable liquid formulation of melphalan comprising melphalan in an amount of about 0.1% w/w to about 10% w/w of the formulation, a non-aqueous liquid in an amount of about 45% w/w to about 98% w/w of the formulation, the non-aqueous liquid comprising a first solvent; and antioxidant in an amount of about 0.001% w/w to about 1% w/w of the formulation, an organic acid in an amount of about 0.02% w/w to about 1.5% w/w of the formulation; and a source of chloride ions in an amount of about 0.05% w/w to about 15% w/w of the formulation. The US '148 Application in Example-1 discloses the liquid formulations of melphalan, where one formulation contains melphalan 1% and Polyethylene glycol 99% without any stabilizers. The formulation of melphalan which does not contain stabilizers are detected with significant impurities after 72 hours when stored at 2° C.-8° C. The other formulations which comprise the antioxidant, organic acid (citric acid) and chloride ions source (sodium chloride) have shown the unexpected result that antioxidant, organic acid and chloride ion source combination can stabilize melphalan for a prolonged period of time at 25° C. and 40° C.

US Patent Application No. 2018/0193255 (US '255 Application) discloses the stable liquid parenteral formulation consisting essentially of melphalan hydrochloride, one or more solvents selected from dimethyl acetamide, polyethylene glycol, ethanol, propylene glycol and glycerine and anti-oxidants selected from monothioglycerol and L-cysteine wherein the formulation is free of organic acid and added chloride ions. US '355 Application further discloses that surprisingly there is no significant increase in total impurities at 25° C./60% RH with the liquid formulation of melphalan comprising of one or more solvents selected from DMA, ethanol, PEG and propylene glycol in the presence of the anti-oxidant.

The inventors of the present application have developed a ready-to-dilute liquid formulation of melphalan which overcomes the disadvantages reported in the prior art. The present inventors have unexpectedly discovered that the ready-to-dilute liquid formulation consisting of melphalan and one or more solvents selected from group consisting dimethyl acetamide, polyethylene glycol, ethanol, propylene glycol, dimethyl sulfoxide, N-methylpyrrolidone and glycerol, wherein formulation is free of antioxidants, organic acid and added chloride ions is stable for at least 6 months when stored at 2° C.-8° C.

SUMMARY OF THE INVENTION

The present invention relates to the stable, non-aqueous ready-to-dilute liquid formulation consisting essentially of melphalan, or a pharmaceutical acceptable salt thereof; and one or more solvents selected from group consisting of dimethyl acetamide, polyethylene glycol, ethanol, propylene glycol, dimethyl sulfoxide, N-methylpyrrolidone and glycerol; wherein said formulation is free of antioxidants, organic acid and added chloride ions.

The present invention further relates to a stable, non-aqueous liquid, formulation consisting essentially of melphalan, or a pharmaceutical acceptable salt thereof; and one or more solvents selected from group consisting of dimethyl acetamide, polyethylene glycol, ethanol, propylene glycol, dimethyl sulfoxide, N-methylpyrrolidone and glycerol; wherein said formulation is free of antioxidants, organic acid and added chloride ions; and wherein said formulation, following dilution with a pharmaceutically acceptable diluent, is suitable for injection into a patient. The melphalan salt particularly used in the present invention is melphalan hydrochloride.

The present invention also relates to a stable, non-aqueous liquid, formulation consisting essentially of about 1 mg/ml to about 20 mg/ml of melphalan, or a pharmaceutical acceptable salt thereof; solubilized in about 20% (v/v) to about 50% (v/v) of propylene glycol, about 5% (v/v) to about 25% (v/v) of polyethylene glycol and about 20% (v/v) to about 50% (v/v) of ethanol; wherein said formulation is free of antioxidants, organic acid and added chloride ions; and wherein said formulation, following dilution with a pharmaceutically acceptable diluent, is suitable for injection into a patient.

The present invention specifically relates to a stable, non-aqueous liquid, formulation consisting of about 10 mg/ml of melphalan or pharmaceutically acceptable salt thereof; solubilized in about 40% (v/v) of propylene glycol, about 20% (v/v) of polyethylene glycol and about 40% (v/v) of ethanol; wherein said formulation is free of antioxidants, organic acid and added chloride ions; and wherein said formulation following dilution with a pharmaceutically acceptable diluent, is suitable for injection into a patient.

DETAILED DESCRIPTION OF THE INVENTION

In the context of this invention "melphalan" refers to the pharmaceutically acceptable salts, solvates, hydrates and anhydrous forms thereof, preferably melphalan hydrochloride.

As used herein, the term "about" is defined as ±10%, preferably 15%.

The term "substantial" or "substantially" as used to describe percentage of melphalan hydrochloride in the formulation is at least 90%, or at least about 95%, or at least of 99%.

The term "ready-to-dilute" or RID composition is a stable liquid composition of melphalan hydrochloride that is diluted with suitable diluent for parenteral administration. Suitable diluents may include sterile water for injection, 0.9% sodium chloride, 0.45% sodium chloride, 5% dextrose or combinations thereof.

The term "stable" or "stability" as used herein relate to both physical and chemical stability, wherein pharmaceutical composition of melphalan hydrochloride can be stored for commercially significant periods, such as at least 3 moths, 6 months, one year or two years or 3 years without significant physical instability (description and clarity etc) and chemical degradation. Liquid formulations of the present invention are stable over the course of a typical commercial storage period. The term "stable" can further means as no more than about a 10% loss of melphalan under typical commercial storage conditions. Preferably, formulations of the present inventions will have no more than about a 10% loss of melphalan, more preferably, no more than about a 5% loss of melphalan, under typical commercial storage conditions.

The stable may represent stability when stored at 2° C.-8° C., or at ambient conditions (e.g 25° C.) or elevated temperatures (e.g 40° C.). Percent degradation may be determined by analysing impurities by suitable analytical method.

The term "formulation" refers to pharmaceutical dosage forms containing compositions of melphalan hydrochloride. The pharmaceutical formulations of the present invention can be prepared as solutions or suspensions or dispersions and so on presented in glass ampoules or glass vials or any suitable devices.

In one embodiment, the present invention provides the stable, non-aqueous ready-to-dilute liquid formulation consisting essentially of melphalan, or a pharmaceutical acceptable salt thereof; and one or more solvents; wherein said formulation is free of antioxidants, organic acid and added chloride ions.

Suitable solvents include but not limited to dimethyl acetamide, polyethylene glycol, ethanol, propylene glycol, dimethyl sulfoxide, N-methylpyrrolidone and glycerol.

In another embodiment, the present invention provides the stable, non-aqueous ready-to-dilute liquid formulation consisting essentially of melphalan, or a pharmaceutical acceptable salt thereof; and one or more solvents selected from group consisting of dimethyl acetamide, polyethylene glycol, ethanol, propylene glycol, dimethyl sulfoxide, N-methylpyrrolidone and glycerol; wherein said formulation is free of antioxidants, organic acid and added chloride ions.

In yet another embodiment, the present invention provides the stable, non-aqueous liquid, formulation consisting essentially of melphalan, or a pharmaceutical acceptable salt thereof; and one or more solvents selected from group consisting of dimethyl acetamide, polyethylene glycol, ethanol, propylene glycol, dimethyl sulfoxide, N-methylpyrrolidone and glycerol; wherein said formulation is free of antioxidants, organic acid and added chloride ions; and wherein said formulation, following dilution with a pharmaceutically acceptable diluent, is suitable for injection into a patient.

In an embodiment of the invention the present invention provides the stable, non-aqueous liquid, formulation consisting essentially of about 1 mg/ml to about 20 mg/ml of melphalan, or a pharmaceutical acceptable salt thereof; solubilized in about 20% (v/v) to about 50% (v/v) of propylene glycol, about 5% (v/v) to about 25% (v/v) of polyethylene glycol and about 20% (v/v) to about 50% (v/v) of ethanol; wherein said formulation is free of antioxidants, organic acid and added chloride ions; and wherein said formulation, following dilution with a pharmaceutically acceptable diluent, is suitable for injection into a patient.

In the specific embodiment of the present invention provides the stable, non-aqueous liquid, formulation consisting of about 10 mg/ml of melphalan or pharmaceutically acceptable salt thereof; solubilized in about 40% (v/v) of propylene glycol, about 20% (v/v) of polyethylene glycol and about 40% (v/v) of ethanol; wherein said formulation is free of antioxidants, organic acid and added chloride ions; and wherein said formulation following dilution with a pharmaceutically acceptable diluent, is suitable for injection into a patient.

Experiments to produce commercially viable polyethylene glycol preparations have been performed. Solution of melphalan hydrochloride with 99% of polyethylene glycol without any stabilizers as disclosed in US '148 patent application degraded to non-melphalan products over a time. As such an 100% polyethylene glycol formulations is not feasible for pharmaceutical purposes.

It has been determined that the pharmaceutically liquid formulations of melphalan or a pharmaceutical acceptable salt thereof, in particular melphalan hydrochloride can be prepared by combining with one or more solvents selected from group consisting of dimethyl acetamide, polyethylene glycol, ethanol, propylene glycol, dimethyl sulfoxide, N-methylpyrrolidone and glycerol. Particularly preferred solvents include polyethylene glycol, propylene glycol and ethanol or mixtures thereof.

It has been surprisingly discovered that stable liquid formulations of melphalan hydrochloride can be obtained by solubilizing melphalan hydrochloride in polyethylene glycol, propylene glycol and ethanol (dehydrated alcohol) mixture. Without wishing to be held to any particular theory, it is surprisingly found that melphalan hydrochloride solubilized in mixture of polyethylene glycol, propylene glycol and ethanol solvents is typically stored at commercial storage conditions.

Typical commercial storage conditions include time periods of, for example, about 30 days, about 90 days, about 180 days, and about 365 days (about 1 month, about 3 months, about 6 months, and about 1 year). Typical commercial storage conditions also include temperatures of about 25° C. (ambient room temperature) and refrigerated temperatures below ambient room temperature, for example, about 5° C. Preferably, the liquid formulations of the present invention are stored at refrigerated temperatures.

Such formulations will typically comprise less than 60% (v/v) of propylene glycol. In embodiment of the invention, the formulation will comprise of about 20% (v/v) to about 50% (v/v) of propylene glycol, more preferably of about 25% (v/v) to about 45% (v/v) of propylene glycol and most preferably of about 40% (v/v) of propylene glycol.

In embodiments of the invention formulations will comprise of less than 30% (v/v) of polyethylene glycol, more preferably of about 5% (v/v) to about 25% (v/v) of polyethylene glycol and most preferably of about 20% (v/v) of polyethylene glycol.

In embodiments of the invention formulations will comprise of less than 60% (v/v) of ethanol (dehydrated alcohol). In further embodiment of the invention, the formulation will comprise of about 20% (v/v) to about 50% (v/v) of ethanol, more preferably of about 25% (v/v) to about 45% (v/v) of ethanol and most preferably of about 40% (v/v) of ethanol.

Melphalan hydrochloride is highly unstable in presence of moisture/water content or temperature. Three known impurities namely impurity-1, impurity-2 and impurity-3 are present as shown below a) Impurity-1 (dihydroxy melphalan) is a hydrolytic impurity and it is chemically (S)-2-amino-3-(4-(bis(2-hydroxy ethyl) aminophenyl) propanoic acid and represented by following structure

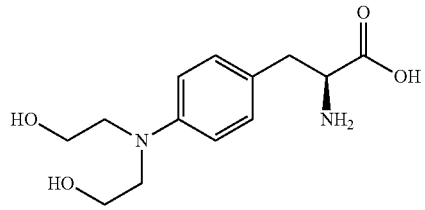 [SMILES: N[C@@H](Cc1ccc(N(CCO)CCO)cc1)C(=O)O]

b) Impurity-2 (monohydroxy melphalan) is a hydrolytic impurity and it is chemically (S)-2-amino-3-(4-((2-chloroethyl) (2-hydroxyethyl) amino) phenyl) propanoic acid and represented by following structure

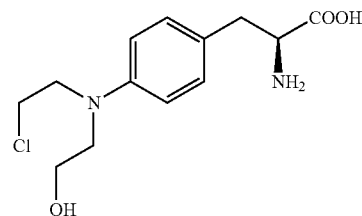 [SMILES: N[C@@H](Cc1ccc(N(CCO)CCCl)cc1)C(=O)O]

c) Impurity-3 (Melphalan dimer) is chemically represented as 4-[[2-[[4-[bis(2-chloroethyeaminc]-L-phenylalanyl]oxy]ethyl](2-chloroethyl) amino]-L-phenylalanine,trifluoroacetate salt and is represented by following structure

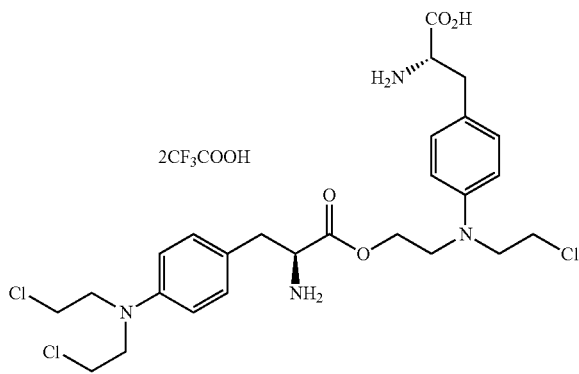 [SMILES: N[C@@H](Cc1ccc(N(CCCl)CCOC(=O)[C@@H](N)Cc2ccc(N(CCCl)CCCl)cc2)cc1)C(=O)O]

In embodiments of the invention, the invention provides stable, non-aqueous liquid, formulation consisting essentially of about 1 mg/ml to about 20 mg/ml of melphalan, or a pharmaceutical acceptable salt thereof; solubilized in about 20% (v/v) to about 50% (v/v) of propylene glycol, about 5% (v/v) to about 25% (v/v) of polyethylene glycol and about 20% (v/v) to about 50% (v/v) of ethanol; wherein said formulation is free of antioxidants, organic acid and added chloride ions; and wherein each individual impurity of dihydroxy melphalan or monohydroxy melphalan impurity is less than about 2.0%, more preferably less than about 1.0% when stored at 2° C.-8° C. for at least 6 months.

In further embodiments of the invention, the invention provides stable, non-aqueous liquid, formulation consisting essentially of about 1 mg/ml to about 20 mg/ml of melphalan, or a pharmaceutical acceptable salt thereof; solubilized in about 20% (v/v) to about 50% (v/v) of propylene glycol, about 5% (v/v) to about 25% (v/v) of polyethylene glycol and about 20% (v/v) to about 50% (v/v) of ethanol; wherein said formulation is free of antioxidants, organic acid and added chloride ions; and wherein melphalan related impurities is less than about 5.0%, preferably less than 3.0% and more preferably less than 2.0% when stored at 2° C.-8° C. for at least 6 months.

In embodiments, the present invention provides the stable, non-aqueous liquid, formulation consisting of about 10 mg/ml of melphalan or pharmaceutically acceptable salt thereof; solubilized in about 40% (v/v) of propylene glycol, about 20% (v/v) of polyethylene glycol and about 40% (v/v) of ethanol; wherein said formulation is free of antioxidants, organic acid and added chloride ions; and wherein each individual impurity of dihydroxy melphalan or monohydroxy melphalan impurity is less than about 2.0%, more preferably less than about 1.0% when stored at 2° C.-8° C. for at least 6 months.

In embodiments, the present invention provides the stable, non-aqueous liquid, formulation consisting of about 10 mg/ml of melphalan or pharmaceutically acceptable salt thereof; solubilized in about 40% (v/v) of propylene glycol, about 20% (v/v) of polyethylene glycol and about 40% (v/v) of ethanol; wherein said formulation is free of antioxidants, organic acid and added chloride ions; and wherein melphalan related impurities is less than about 5.0%, preferably less than 3.0% and more preferably less than 2.0% when stored at 2° C.-8° C. for at least 6 months.

Formulations of the present invention can comprise pharmaceutically useful concentrations of melphalan, or a pharmaceutically acceptable salt thereof. Useful concentrations include concentrations ranging from about 0.3 mg/mL to about 25 mg/mL. Preferably, the concentration of melphalan, or a pharmaceutically acceptable salt thereof, ranges from about 0.4 mg/mL to about 20 mg/mL. Preferred concentrations for ready-to-dilute include about 1 mg/mL, about 2 mg/mL, about 5 mg/mL, about 7.5 mg/mL, about 10 mg/mL, about 12.5 mg/mL, about 15 mg/mL, about 17.5 mg/mL and about 20 mg/mL of melphalan or a pharmaceutically acceptable salt thereof.

Also within the scope of the invention are methods of treating diseases in patients with multiple myeloma for whom oral therapy is not appropriate and used as a high-dose conditioning treatment prior to hematopoietic progenitor (stem) cell transplantation in patients with multiple myeloma. These methods comprise administering to the patient a therapeutically effective amount of a preparation prepared from a pharmaceutical formulation of the present invention. The term "therapeutically effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

The liquid formulations of melphalan described herein are intended to be administered via injection, for example, they may be administered subcutaneously, intracutaneously, intravenously, intramuscularly, intra-articularly, intrasynovially, intrasternally, intrathecally, intralesionally, intracranially or via infusion. In a typical preparation, the volume of the liquid formulation of the present invention needed for the required dose can be aseptically withdrawn and transferred to an infusion bag of 0.9% Sodium Chloride (or other pharmaceutically acceptable intravenous solution) for injection. After transfer, the contents of the infusion bag are thoroughly mixed. Administration by intravenous infusion is typically provided over a time period of from about 15 to about 60 minutes. Previously described lyophilized formulations of melphalan required reconstitution of the lyophilized melphalan hydrochloride prior to mixture with the acceptable intravenous solution before infusion.

The invention is further illustrated by the following examples, which are not construed to be limiting the scope of the invention.

| Comparative Examples 1 to 3: | | | | |
|---|---|---|---|---|
| S. No | Ingredients | Comparative Example 1 mg/mL | Comparative Example 2 mg/mL | Comparative Example 3 mg/mL |
| 1 | Melphalan HCl | 11.2 mg (Equivalent to 10 mg melphalan base) | 11.2 mg (Equivalent to 10 mg melphalan base) | 11.2 mg (Equivalent to 10 mg melphalan base) |
| 2 | Propylene glycol | 0.3 mL | 0.5 mL | 0.7 mL |
| 3 | Polyethylene glycol | 0.7 mL | 0.5 mL | 0.3 mL |
| 4 | Nitrogen | Q.S | Q.S | Q.S |

Manufacturing Process:

Melphalan hydrochloride was added to manufacturing vessel containing propylene glycol and stirred to which polyethylene glycol was added to and stirred to get homogenous solution. The homogenous solution was filtered through 0.2 μm filter and filled into vials under nitrogen and sealed.

Melphalan hydrochloride solutions prepared according to the above comparative examples was tested for stability at various stability conditions such as 2° C.-8° C. for a period of 6 months. Stability data is summarized in Table-1, 2 and 3 with respect to the comparative examples 1, 2 and 3.

TABLE - 1

Stability data for the product as obtained in Comparative Example - 1.

| Condition/ | | 2-8° C. | | |
|---|---|---|---|---|
| Time Point | Initial | 1 M | 3 M | 6 M |
| Assay | 99.5% | 98.1% | 96.2% | 89.6% |
| Impurity - 1 (dihydroxy melphalan) | 0.005% | 0.3% | 0.6% | 1.2% |
| Impurity - 2 (monohydroxy melphalan) | 0.08% | 1.5% | 2.7% | 4.9% |
| Impurity - 3 (dimer) | 0.03% | 0.06% | 0.09% | 0.2% |
| Total Impurities | 0.6% | 2.3% | 5.6% | 9.6% |

TABLE - 2

Stability data for the product as obtained in Comparative Example - 2.

| Condition/ | 2-8° C. | | | |
|---|---|---|---|---|
| Time Point | Initial | 1 M | 3 M | 6 M |
| Assay | 99.8% | 98.6% | 96.5% | 92.3% |
| Impurity - 1 (dihydroxy melphalan) | 0.003% | 0.2% | 0.5% | 1.1% |
| Impurity - 2 (monohydroxy melphalan) | 0.09% | 1.1% | 1.8% | 3.2% |
| Impurity - 3 (dimer) | 0.02% | 0.03% | 0.06% | 0.17% |
| Total Impurities | 0.35% | 1.9% | 4.5% | 7.2% |

TABLE - 3

Stability data for the product as obtained in Comparative Example - 3.

| Condition/ | 2-8° C. | | | |
|---|---|---|---|---|
| Time Point | Initial | 1 M | 3 M | 6 M |
| Assay | 100.2% | 99.4% | 98.1% | 96.4% |
| Impurity - 1 (dihydroxy melphalan) | 0.004% | 0.02% | 0.45% | 0.9% |
| Impurity - 2 monohydroxy melphalan) | 0.12% | 0.25% | 1.2% | 2.3% |
| Impurity - 3 (dimer) | 0.04% | 0.07% | 0.1% | 0.15% |
| Total Impurities | 0.45% | 0.9% | 2.3% | 5.8% |

Examples 1 to 3

| S. No | Ingredients | Example 1 mg/mL | Example 2 mg/mL | Example 3 mg/mL |
|---|---|---|---|---|
| 1 | Melphalan HCl | 11.2 mg (Equivalent to 10 mg melphalan base) | 11.2 mg (Equivalent to 10 mg melphalan base) | 11.2 mg (Equivalent to 10 mg melphalan base) |
| 2 | Propylene glycol | 0.1 mL | 0.2 mL | 0.25 mL |
| 3 | Polyethylene glycol | 0.1 mL | 0.2 mL | 0.25 mL |
| 4 | Ethanol | 0.8 mL | 0.6 mL | 0.5 mL |
| 5 | Nitrogen | Q.S | Q.S | Q.S |

Manufacturing Process

Melphalan hydrochloride was added to manufacturing vessel containing propylene glycol and stirred to which ethanol (dehydrated) was added to and stirred to get a clear solution and then polyethylene glycol was added to the clear solution to form the homogenous solution. The homogenous solution was filtered through 0.2 µm filter and filled into vials under nitrogen and sealed.

Melphalan hydrochloride solutions prepared according to the above examples 1, 2 and 3 was tested for stability at various stability conditions such as 2° C.-8° C. for a period of 6 months. Stability data is summarized in Table-4, 5 and 6 with respect to the examples 1, 2 and 3.

TABLE - 4

Stability data for the product as obtained in Example - 1.

| Condition/ | 2-8° C. | | | |
|---|---|---|---|---|
| Time Point | Initial | 1 M | 3 M | 6 M |
| Assay | 99.8% | 98.6% | 97.5% | 96.2% |
| Impurity - 1 (dihydroxy melphalan) | 0.09% | 0.12% | 0.48% | 0.8% |
| Impurity - 2 (monohydroxy melphalan) | 0.09% | 0.8% | 1.3% | 2.5% |
| Impurity - 3 (dimer) | 0.03% | 0.04% | 0.05% | 0.09% |
| Total Impurities | 0.45% | 1.6% | 3.2% | 4.6% |

TABLE - 5

Stability data for the product as obtained in Example - 2.

| Condition/ | 2-8° C. | | | |
|---|---|---|---|---|
| Time Point | Initial | 1 M | 3 M | 6 M |
| Assay | 100.1% | 98.9% | 97.3% | 96.6% |
| Impurity - 1 (dihydroxy melphalan) | 0.009% | 0.08% | 0.5% | 0.9% |
| Impurity - 2 (monohydroxy melphalan) | 0.08% | 0.7% | 1.6% | 2.8% |
| Impurity - 3 (dimer) | 0.033% | 0.04% | 0.06% | 0.08% |
| Total Impurities | 0.45% | 1.6% | 2.9% | 4.2% |

TABLE - 6

Stability data for the product as obtained in Example - 3.

| Condition/ | 2-8° C. | | | |
|---|---|---|---|---|
| Time Point | Initial | 1 M | 3 M | 6 M |
| Assay | 99.9% | 99.3% | 98.6% | 98.2 |
| Impurity - 1 (dihydroxy melphalan) | 0.02% | 0.05% | 0.09% | 0.13% |
| Impurity - 2 (monohydroxy melphalan) | 0.09% | 0.16% | 0.45% | 0.59% |
| Impurity - 3 (dimer) | 0.038% | 0.015% | 0.03% | 0.06% |
| Total Impurities | 0.46% | 0.86% | 1.45% | 1.9% |

Examples 4 to 6

| S. No | Ingredients | Example 4 mg/mL | Example 5 mg/mL | Example 6 mg/mL |
|---|---|---|---|---|
| 1 | Melphalan HCl | 11.2 mg (Equivalent to 10 mg melphalan base) | 11.2 mg (Equivalent to 10 mg melphalan base) | 11.2 mg (Equivalent to 10 mg melphalan base) |
| 2 | Propylene glycol | 0.4 mL | 0.5 mL | 0.6 mL |
| 3 | Polyethylene glycol | 0.2 mL | 0.2 mL | 0.2 mL |
| 4 | Ethanol | 0.4 mL | 0.3 mL | 0.2 mL |
| 5 | Nitrogen | Q.S | Q.S | Q.S |

The manufacturing process for the preparations of Example 4, 5 and 6 is same as disclosed in example 1, 2 and 3. Melphalan hydrochloride solutions prepared according to the above examples 4, 5 and 6 was tested for stability at various stability conditions such as 2° C.-8° C. for a period of 6 months. Stability data is summarized in Table-7, 8 and 9 with respect to the examples 4, 5 and 6.

TABLE - 7

Stability data for the product as obtained in Example - 4.

| Condition/ | | 2-8° C. | | |
|---|---|---|---|---|
| Time Point | Initial | 1 M | 3 M | 6 M |
| Assay | 100.3% | 100.1% | 99.8% | 99.9% |
| Impurity - 1 (dihydroxy melphalan) | 0.005% | 0.005% | 0.005% | 0.005% |
| Impurity - 2 (monohydroxy melphalan) | 0.03% | 0.08% | 0.090% | 0.15% |
| Impurity - 3 (dimer) | 0.033% | 0.033% | 0.033% | 0.044% |
| Total Impurities | 0.43% | 0.65% | 0.9% | 1.08% |

TABLE - 8

Stability data for the product as obtained in Example - 5.

| Condition/ | | 2-8° C. | | |
|---|---|---|---|---|
| Time Point | Initial | 1 M | 3 M | 6 M |
| Assay | 100.2% | 99.5% | 98.4% | 98.2% |
| Impurity - 1 (dihydroxy melphalan) | 0.005% | 0.06% | 0.08% | 0.13% |
| Impurity - 2 (monohydroxy melphalan) | 0.039% | 0.19% | 0.23% | 0.45% |
| Impurity - 3 (dimer) | 0.036% | 0.02% | 0.04% | 0.06% |
| Total Impurities | 0.65% | 0.9% | 1.5% | 1.6% |

TABLE - 9

Stability data for the product as obtained in Example - 6.

| Condition/ | | 2-8° C. | | |
|---|---|---|---|---|
| Time Point | Initial | 1 M | 3 M | 6 M |
| Assay | 100.5% | 99.3% | 98.4% | 96.5% |
| Impurity - 1 (dihydroxy melphalan) | 0.009% | 0.1% | 0.26% | 0.43% |
| Impurity - 2 (monohydroxy melphalan) | 0.09% | 0.89% | 1.63% | 2.32% |
| Impurity - 3 (dimer) | 0.03% | 0.04% | 0.05% | 0.09% |
| Total Impurities | 0.72% | 1.9% | 2.6% | 3.2% |

Example 7—In-Use Studies of Formulations

Admixtures in 0.9% sodium chloride were of example-4 were prepared to a dose of 0.45 mg/mL and purity was determined over time at room temperature for upto 4 hours using HPLC. The formulation of example containing 40% (v/v) propylene glycol, 20% (v/v) polyethylene glycol and 40% (v/v) of ethanol had a concentration of 10 mg/mL of melphalan, so that 5 mL was injected into 0.9% sodium chloride bag to a final concentration of 0.45 mg/mL and sampled at room temperature after 4 hours. After 4 hours the purity was 95.8%. This is within the label requirements for dosing Evomela®. This formulation of the present invention could be used for up to 4 hours at room temperature. The comparative Evomela® admixture purity was 95.0% after 4 hours at 25° C.

As those skilled in the art will appreciate, numerous modifications and variations of the present invention are possible in view of the above teachings. It is therefore understood that within the scope of the appended claims, the invention can be practiced otherwise than as specifically described herein, and the scope of the invention is intended to encompass all such variations.

The invention claimed is:

1. A stable, non-aqueous liquid, ready-to-dilute formulation consisting of about 1 mg/ml to about 20 mg/ml of melphalan hydrochloride; solubilized in about 20% (v/v) to about 50% (v/v) of propylene glycol, about 5% (v/v) to about 25% (v/v) of polyethylene glycol and about 20% (v/v) to about 50% (v/v) of ethanol; wherein said formulation is free of antioxidants, organic acid and added chloride ions.

2. A method of treating multiple myeloma comprising providing a liquid, pharmaceutical formulation of claim 1; diluting the liquid formulation with a pharmaceutically acceptable injectable diluent to form an injectable pharmaceutical preparation; administering the injectable pharmaceutical preparation to a patient in need of treatment thereof.

3. A stable, non-aqueous liquid, formulation consisting of about 10 mg/ml of melphalan or pharmaceutically acceptable salt thereof; solubilized in about 40% (v/v) of propylene glycol, about 20% (v/v) of polyethylene glycol and about 40% (v/v) of ethanol; wherein said formulation is free of antioxidants, organic acid and added chloride ions; and wherein said formulation following dilution with a pharmaceutically acceptable diluent, is suitable for injection into a patient.

4. The formulation of claim 3, wherein melphalan is melphalan hydrochloride.

5. A method of treating multiple myeloma comprising providing a liquid, pharmaceutical formulation of claim 3; diluting the liquid formulation with a pharmaceutically acceptable injectable diluent to form an injectable pharmaceutical preparation; administering the injectable pharmaceutical preparation to a patient in need of treatment thereof.

* * * * *